(12) United States Patent
Nishina et al.

(10) Patent No.: US 11,076,749 B2
(45) Date of Patent: Aug. 3, 2021

(54) ENDOSCOPE

(71) Applicant: OLYMPUS CORPORATION, Tokyo (JP)

(72) Inventors: Kenichi Nishina, Hachioji (JP); Teppei Tsuruta, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 282 days.

(21) Appl. No.: 16/132,571

(22) Filed: Sep. 17, 2018

(65) Prior Publication Data
US 2019/0014978 A1  Jan. 17, 2019

Related U.S. Application Data

(63) Continuation of application No. PCT/JP2016/085954, filed on Dec. 2, 2016.

(30) Foreign Application Priority Data

Mar. 23, 2016 (JP) .............................. JP2016-059130

(51) Int. Cl.
*A61B 1/00* (2006.01)
*A61B 1/05* (2006.01)
(Continued)

(52) U.S. Cl.
CPC .................. *A61B 1/05* (2013.01); *A61B 1/00* (2013.01); *A61B 1/00009* (2013.01);
(Continued)

(58) Field of Classification Search
CPC ......... A61B 1/05; A61B 8/12; A61B 1/00163; A61B 1/00009; A61B 1/00;
(Continued)

(56) References Cited

U.S. PATENT DOCUMENTS

2008/0119738 A1* 5/2008 Imahashi ............. A61B 1/0055
600/462
2008/0300457 A1* 12/2008 Hosaka .................... A61B 1/12
600/110
(Continued)

FOREIGN PATENT DOCUMENTS

| JP | S57-9442 A | 1/1982 |
| JP | 2005-342129 A | 12/2005 |
| JP | 2006-212353 A | 8/2006 |

OTHER PUBLICATIONS

International Search Report dated Feb. 28, 2017 issued in PCT/JP2016/085954.

*Primary Examiner* — John P Leubecker
*Assistant Examiner* — Sung Ham
(74) *Attorney, Agent, or Firm* — Scully, Scott, Murphy & Presser, P.C.

(57) ABSTRACT

An endoscope includes: an insertion portion to be inserted into a subject; an image sensor provided at a distal end of the insertion portion and configured to acquire an image of the subject; a signal cable connected to the image sensor at one end of the signal cable, the signal cable including a signal line group formed of a plurality of signal lines configured to transmit signals acquired by the image sensor; a tube provided at a part of the signal cable, the tube covering the signal cable and having insulation properties; and a filling member configured to fill a vacant space formed between the signal cable and the tube and at least a part of which is made of a material with low melting point.

12 Claims, 10 Drawing Sheets

(51) Int. Cl.
 *A61B 8/12* (2006.01)
 *A61B 1/04* (2006.01)
 *G02B 23/24* (2006.01)
(52) U.S. Cl.
 CPC ............ *A61B 1/00163* (2013.01); *A61B 1/04* (2013.01); *A61B 8/12* (2013.01); *G02B 23/2423* (2013.01)
(58) Field of Classification Search
 CPC ............ A61B 1/00018; A61B 1/00071; A61B 1/0011; A61B 1/00112; A61B 1/00119; A61B 1/0057; A61B 1/04; G02B 23/2423
 USPC .................................................. 600/100, 140
 See application file for complete search history.

(56) References Cited

U.S. PATENT DOCUMENTS

| | | | | |
|---|---|---|---|---|
| 2009/0198106 | A1* | 8/2009 | Ichihashi | ................. A61B 1/05 600/178 |
| 2014/0100463 | A1* | 4/2014 | Sekiguchi | .............. A61B 1/018 600/462 |
| 2017/0086660 | A1* | 3/2017 | Igarashi | ................. H05K 3/361 |
| 2018/0310813 | A1* | 11/2018 | Igarashi | ................. A61B 1/051 |

\* cited by examiner

ENDOSCOPE

CROSS-REFERENCE TO RELATED APPLICATION

This application is a continuation of PCT international application Ser. No. PCT/JP2016/085954 filed on Dec. 2, 2016 which designates the United States, incorporated herein by reference, and which claims the benefit of priority from Japanese Patent Applications No. 2016-059130, filed on Mar. 23, 2016, incorporated herein by reference.

BACKGROUND

The present disclosure relates to an endoscope.

In the related art, a rigid or flexible endoscope is used at the time of observing organs or materials of a subject, such as a patient. For example, an operator, such as a doctor, uses an endoscope in which an ultrasound transducer that sends and receives ultrasound waves is provided at a distal end of an insertion portion and observes an observation target on the basis of information that is related to characteristics of the observation target and that is generated based on ultrasound echoes received from the ultrasound transducer.

The ultrasound transducer includes a plurality of piezoelectric elements, each of which converts an electrical pulse signal to an ultrasound pulse (acoustic pulse), applies the ultrasound pulse to the observation target, converts an ultrasound echo reflected by the observation target to an electrical echo signal, and outputs the electrical echo signal. Each of the piezoelectric elements is electrically connected to an ultrasound observation device via a cable that includes a plurality of signal lines.

Incidentally, there is a demand to reduce a diameter of the insertion portion of the endoscope. As a technology for reducing the diameter of the insertion portion, there is a known technology for dividing some of the plurality of signal lines in the cable into a plurality of bundles, thus avoiding interference between the cable and internal objects other than the cable (for example, see Japanese Laid-open Patent Publication No. 2005-342129).

Furthermore, as a technology for preventing disconnection of wiring lines between an ultrasound transducer and a cable, there is a known technology for collectively covering a plurality of signal lines by a heat shrinkable tube and binding the signal lines (for example, see Japanese Laid-open Patent Publication No. 2006-212353).

There is a need for an endoscope in which an operation at the time of maintenance or repair is easily performed while preventing friction generated in the cable.

SUMMARY

An endoscope according to one aspect of the present disclosure includes: an insertion portion to be inserted into a subject; an image sensor provided at a distal end of the insertion portion and configured to acquire an image of the subject; a signal cable connected to the image sensor at one end of the signal cable, the signal cable including a signal line group formed of a plurality of signal lines configured to transmit signals acquired by the image sensor; a tube provided at a part of the signal cable, the tube covering the signal cable and having insulation properties; and a filling member configured to fill a vacant space formed between the signal cable and the tube and at least a part of which is made of a material with low melting point.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
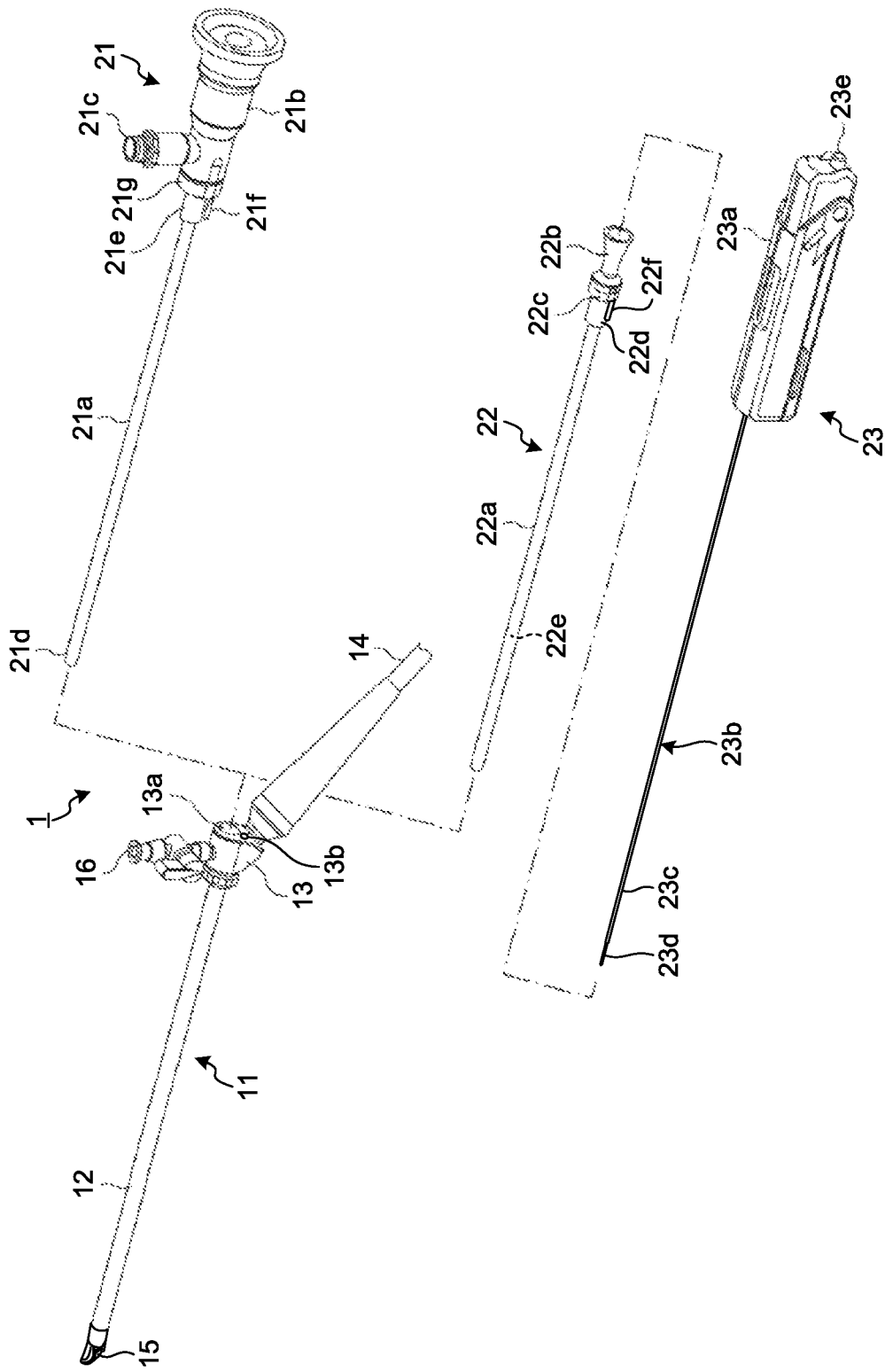
FIG. 1 is a perspective view schematically illustrating a rigid endoscope system according to a first embodiment.

Modes (hereinafter, referred to as "embodiments") for carrying out the present disclosure will be described below with reference to the drawings. The present disclosure is not limited by the embodiments below. Further, in the description of the drawings, the same components are denoted by the same reference numerals.

First Embodiment

Figure 2:
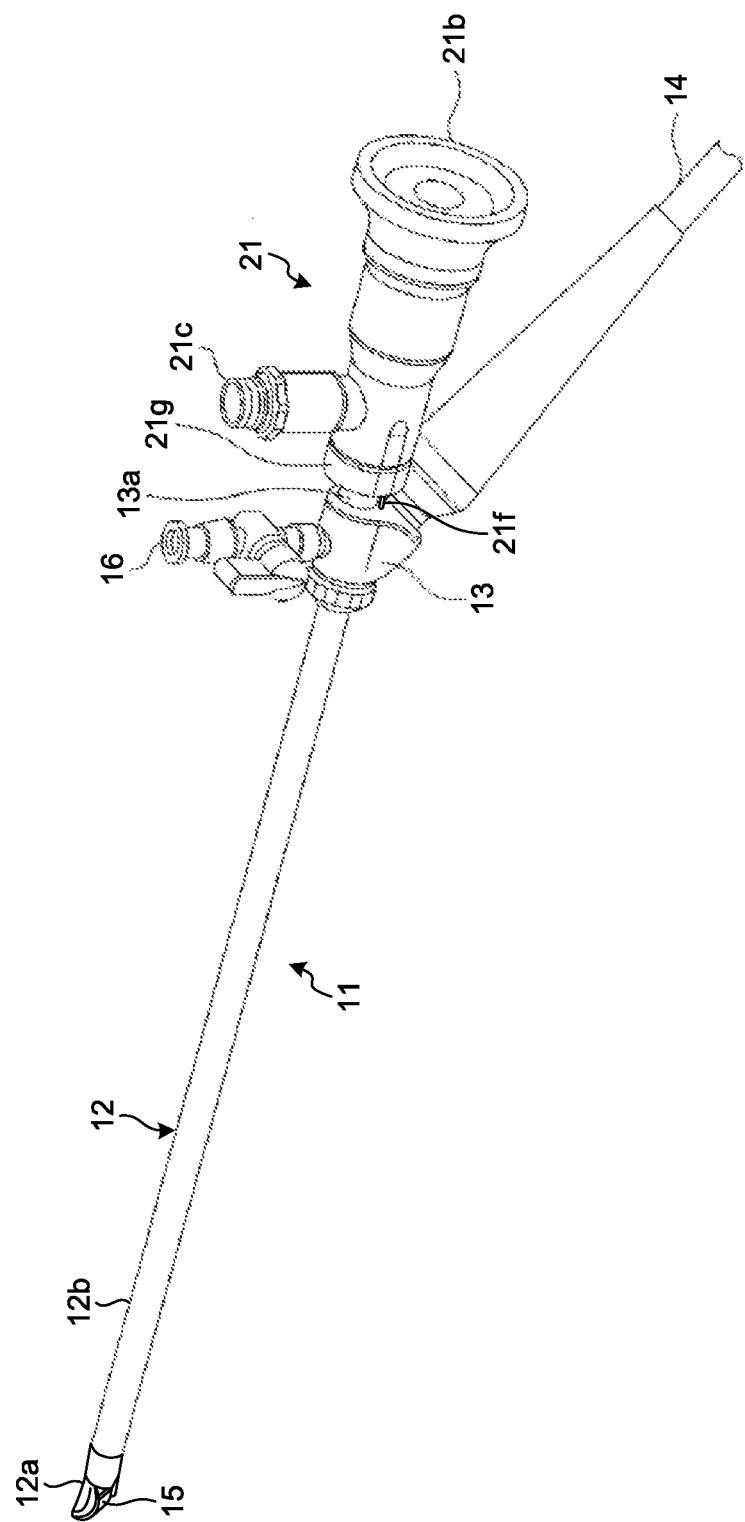
FIG. 2 is a perspective view a configuration in a case where an optical viewing tube is mounted on a rigid endoscope main body of the rigid endoscope system according to the first embodiment.
Figure 3:
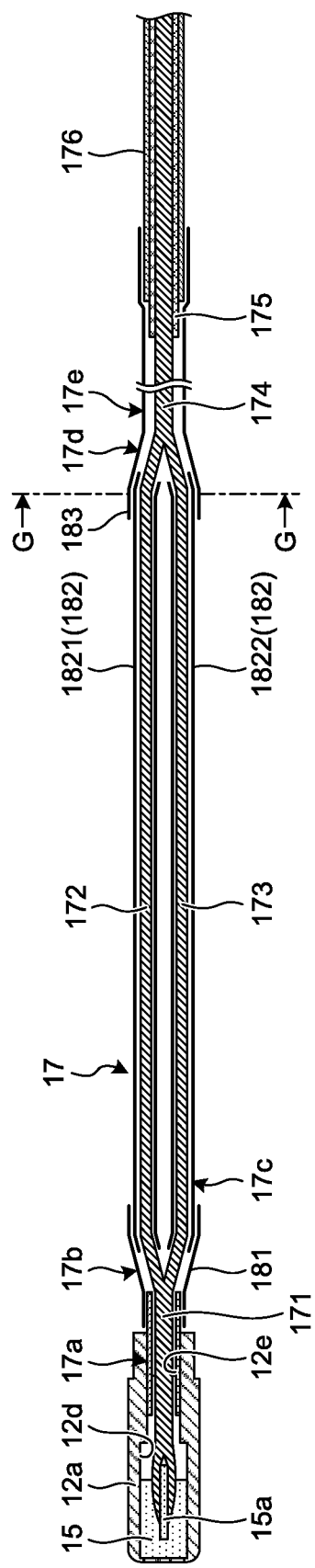
FIG. 3 is a cross-sectional view schematically illustrating a configuration of a relevant part of the rigid endoscope main body of the rigid endoscope system according to the first embodiment.
Figure 4:
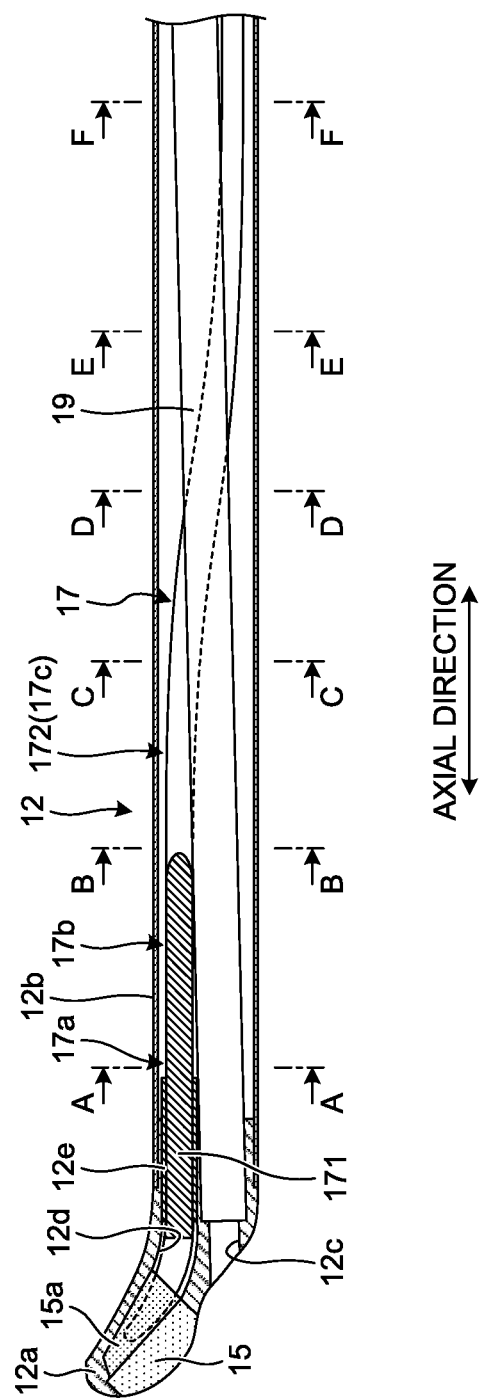
FIG. 4 is a cross-sectional view schematically illustrating a configuration of a distal end of the rigid endoscope main body of the rigid endoscope system according to the first embodiment.

FIG. 1 is a perspective view schematically illustrating a rigid endoscope system according to a first embodiment. FIG. 2 is a perspective view a configuration in a case where an optical viewing tube is mounted on a rigid endoscope main body of the rigid endoscope system according to the first embodiment. FIG. 3 is a cross-sectional view schematically illustrating a configuration of a relevant part of the rigid endoscope main body of the rigid endoscope system according to the first embodiment, and is the cross-sectional view illustrating a configuration in a case where the rigid endoscope body is expanded linearly. FIG. 4 is a cross-sectional view schematically illustrating a configuration of a distal end of the rigid endoscope main body of the rigid endoscope system according to the first embodiment.

A rigid endoscope system 1 is a system that performs ultrasound diagnosis inside a subject, such as a human, using an ultrasound endoscope and is used at the time of, for example, transurethrally sampling biological tissue of the prostate. The rigid endoscope system 1 includes a rigid endoscope main body 11, an optical viewing tube 21 as an imaging device, a treatment instrument guide 22, and a treatment instrument device 23.

The rigid endoscope main body 11 includes a first insertion portion 12 that is inserted into a lumen (for example, a urethra) of the subject, a grip portion 13 that is provided on a proximal side of the first insertion portion 12, and a universal cord 14 that extends from the grip portion 13 on a side opposite to a side at which the first insertion portion 12 is connected. FIG. 2 illustrates a configuration in a case where the optical viewing tube 21 is mounted on the rigid endoscope main body 11 as an example of use modes of the rigid endoscope system 1.

The first insertion portion 12 is a portion that is rigid and extends linearly and through which a signal cable 17 extending from the universal cord 14 is inserted in a lower side of the interior along the axial direction. The first insertion portion 12 includes a distal end component portion 12a that is provided at a distal end of the first insertion portion 12 and that holds an ultrasound transducer 15 that acquires information on the subject and a tubular portion 12b having a tubular shape whose distal end is fitted to a proximal end side of the distal end component portion 12a and whose proximal end is connected to the grip portion 13 (see FIG. 4). Furthermore, at the distal end component portion 12a, a communication hole 12c that holds a first channel 19, which will be described later, and that communicates with the first channel 19 and an mounting portion 12d that is used to mount the ultrasound transducer 15 are formed. At the mounting portion 12d, an insulation pipe 12e through which the signal cable 17 can be inserted is formed.

Furthermore, the ultrasound transducer 15 that is an image sensor for acquiring information on the subject is provided at the distal end of the first insertion portion 12. The ultrasound transducer 15 is constituted by, for example, a convex array ultrasound transducer and to which a distal end portion of the signal cable 17 is connected. The ultrasound transducer 15 includes a plurality of piezoelectric elements that are arrayed along an axial core of the first insertion portion 12 and arranged so as to perform fan-shaped scanning on an extension of the central axis of the first insertion portion 12. The ultrasound transducer 15 uses the piezoelectric elements provided at a distal end portion thereof to convert electrical pulse signals received from a control device, such as a signal processing unit, which will be described later, into ultrasound pulses (acoustic pulses), apply the ultrasound pulses to the subject, convert ultrasound echoes reflected at the subject into electrical echo signals that represents the ultrasound echoes by using variation in voltage, and output the electrical echo signals.

The ultrasound transducer 15 may be any of a convex transducer or a linear transducer. In the first embodiment, a description will be given with the assumption that the ultrasound transducer 15 is a convex ultrasound transducer that includes a plurality of piezoelectric element arranged in an array and that electronically performs scanning by electronically switching the piezoelectric elements that are used for transmission and reception.

Furthermore, although not illustrated, a connector is provided at a proximal end of the universal cord 14 and is connected to the signal processing unit. The signal processing unit transmits a driving signal to the ultrasound transducer 15 via the signal cable 17, processes an ultrasound signal received by the ultrasound transducer 15, generates an ultrasound tomography image, and displays the ultrasound tomography image on a monitor (not illustrated).

Furthermore, a water supply port 16 with a cock is provided in an upper part of the grip portion 13. The water supply port 16 communicates with the first channel 19, which will be described later, and is able to freely supply a perfusion fluid via a perfusion tube (not illustrated). An operator can appropriately supply the perfusion fluid into the first channel 19 by opening the cock of the water supply port 16.

The first channel 19 is provided inside the first insertion portion 12 so as to be inclined with respect to the axial direction of the first insertion portion 12. Specifically, a distal end portion of the first channel 19 is opened at a distal end surface of the first insertion portion 12 on the side opposite to the grip portion 13 side, and a proximal end portion of the first channel 19 is opened at a proximal end surface of the first insertion portion 12 on the grip portion 13 side. The proximal end portion of the first channel 19 is positioned on the water supply port 16 side in the radial direction of the first insertion portion 12 and the distal end portion of the first channel 19 is positioned on the side opposite to the water supply port 16 in the radial direction of the first insertion portion 12. The first channel 19 is a rigid cylindrical member formed by using, for example, stainless or the like. It is preferable that the first channel 19 have the thickness of 0.15 mm to 0.20 mm from the viewpoint of reducing the outer diameter of the first insertion portion 12. Furthermore, in the present specification, a description will be given with the assumption that the straight line passing through each of the centers of an opening on the distal end surface of the first insertion portion 12 on the side opposite to the grip portion 13 side and an opening on the proximal end surface of the first insertion portion 12 on the side opposite to the grip portion 13 side is inclined with respect to the longitudinal axis of the tubular portion 12b.

Furthermore, the grip portion 13 is provided with an insertion guide hole 13a in which a distal end thereof communicates with the first channel 19 and a proximal end thereof is opened at a proximal end surface of the grip portion 13. In this example, a positioning hole 13b is drilled in the proximal end surface of the grip portion 13 and positioning pins protruding from the optical viewing tube 21, which will be described later, and the treatment instrument guide 22 are fitted into the positioning hole 13b. Furthermore, It may be possible to retain the positioning pins using a fixing screw that fixes the positioning pin to the grip portion 13.

Furthermore, a second insertion portion 21a provided in the optical viewing tube 21 and a third insertion portion 22a provided in the treatment instrument guide 22 are selectively inserted in and removed from the first channel 19 of the rigid endoscope main body 11. Both of the second and third insertion portions 21a and 22a are rigid and extend linearly. An inner diameter of the first channel 19 is set to the size that fits an outer diameter of the second insertion portion 21a. In contrast, an outer diameter of the third insertion portion 22a is set to be substantially equal to the outer diameter of the second insertion portion 21a. Furthermore, a small gap through which the perfusion fluid is allowed to flow is secured between an inner circumference of the first channel 19 and an outer circumference of each of the second and third insertion portions 21a and 22a. Thus, the inner diameter of the first channel 19 is set to be slightly greater than the outer diameter of both of the second and third insertion portions 21a and 22a by an amount corresponding to a gap that allows the perfusion fluid to flow.

Furthermore, as illustrated in FIG. 1, an eyepiece portion 21b is provided on a proximal side of the second insertion portion 21a provided in the optical viewing tube 21 and a mouthpiece portion 21c through which a light guide (not illustrated) is inserted is provided in an upper part in the vicinity of a distal end of the eyepiece portion 21b. The light guide passes through the interior of the second insertion portion 21a and extends in the distal end direction, and illumination light transmitted through the light guide is emitted from an illumination window (not illustrated) provided on the distal end portion of the second insertion portion 21a, thereby illuminating a body cavity wall of the subject. Furthermore, an observation window 21d is provided on the distal end of the second insertion portion 21a so as to be adjacent to the illumination window. Light reflected from the body cavity wall of the subject enters the observation window 21d and then a subject image formed on an optical member, such as an objective lens, provided inside the observation window 21d is transmitted to the eyepiece portion 21b through a relay optical system and then observed.

Furthermore, a flange portion 21g is formed on the distal end of the eyepiece portion 21b. A supporting portion 21e protrudes from the center of a distal end surface of the flange portion 21g. Furthermore, a proximal end portion of the second insertion portion 21a is supported by the supporting portion 21e. The distal end surface of the flange portion 21g faces the proximal end surface of the grip portion 13 when the second insertion portion 21a is inserted into the rigid endoscope main body 11 via the insertion guide hole 13a. In this case, the supporting portion 21e is inserted into the insertion guide hole 13a. Furthermore, a positioning pin 21f protrudes from a lower part of the distal end surface of the flange portion 21g. The positioning pin 21f is fitted in the positioning hole 13b having an opening at the proximal end surface of the grip portion 13, thereby movement in a rotation direction is restricted.

The treatment instrument guide 22 includes the third insertion portion 22a, a guiding portion 22b, a flange portion 22c, and a supporting portion 22d. The guiding portion 22b is provided on a proximal side of the third insertion portion 22a and has a funnel shape. Furthermore, the flange portion 22c is formed on the distal end of the guiding portion 22b, the supporting portion 22d protrudes at the center of the distal end surface thereof, and the proximal end portion of the third insertion portion 22a is supported by the supporting portion 22d. The distal end surface of the flange portion 22c faces the proximal end surface of the grip portion 13 when the third insertion portion 22a is inserted into the rigid endoscope main body 11 via the insertion guide hole 13a. In this case, the supporting portion 22d is inserted into the insertion guide hole 13a. Furthermore, a positioning pin 22f protrudes in the lower part of the distal end surface of the flange portion 22c. The positioning pin 22f is fitted in the positioning hole 13b having an opening at the proximal end surface of the grip portion 13 and movement of the positioning hole 13b in the rotation direction is restricted.

A second channel 22e, distal end of which has an opening at the distal end surface of the third insertion portion 22a and a proximal end of which communicates with a guide hole formed in the guiding portion 22b, is provided inside the third insertion portion 22a. An elongated and a rigid treatment instrument 23b that linearly extends forward from a device main body 23a that is provided in the treatment instrument device 23 can be inserted in and removed from the second channel 22e.

The second channel 22e functions as a guide for inserting and removing the treatment instrument 23b and the inner diameter of the second channel 22e is formed to be slightly greater than the outer diameter of the treatment instrument 23b. Furthermore, in the first embodiment, the third insertion portion 22a is formed by using a pipe material, the inside of the third insertion portion 22a is filled with a resin material, and the second channel 22e is formed in the filled resin material. Furthermore, the second channel 22e may also be formed by forming a hole in a solid metallic material used for the third insertion portion 22a.

In the first embodiment, a biopsy device is illustrated as an example of the treatment instrument device 23 and a needle portion of the biopsy device corresponds to the treatment instrument 23b. Thus, in a description below, a description will be given by replacing the treatment instrument device 23 with the biopsy device 23 and replacing the treatment instrument 23b with the needle portion 23b.

The needle portion 23b includes a guide tube needle 23c, which has a smaller outer diameter than the second insertion portion 21a of the optical viewing tube 21, and a biopsy needle 23d and, furthermore, the biopsy needle 23d is inserted into the guide tube needle 23c so as to freely move forward and backward. Furthermore, a pocket is formed on a distal end side of the biopsy needle 23d. When a launch button 23e provided on the back surface of the device main body 23a is pressed, the biopsy needle 23d protrudes forward by receiving a resilient force of a spring that is built in the device main body 23a and is punctured into tissue of the subject, thereby biopsy tissue is taken into the pocket. When the launch button 23e is pressed, the guide tube needle 23c protrudes following the biopsy needle 23d and the biopsy tissue is cut out and taken into the pocket when a distal end of the guide tube needle 23c passes over the pocket.

Because the first channel 19 is arranged at a position protruding toward a scanning surface (observation field of view) of the ultrasound transducer 15, if the needle portion 23b is allowed to protrude forward from the first channel 19, the needle portion 23b passes through the scanning surface of the ultrasound transducer 15; therefore, it is possible to display the needle portion 23b in the ultrasonic tomographic image on the monitor.

The needle portion 23b according to the embodiment is inserted into the first channel 19 via the third insertion portion 22a provided in the treatment instrument guide 22. Thus, if the outer diameter of the third insertion portion 22a is set in accordance with the inner diameter of the first channel 19 and the inner diameter of the second channel 22e formed in the third insertion portion 22a is set in accordance with the outer diameter of the needle portion 23b, it is possible to accurately allow the needle portion 23b that is thinner than the second insertion portion 21a of the optical viewing tube 21 to protrude on the scanning surface of the ultrasound transducer 15.

Figure 5A:
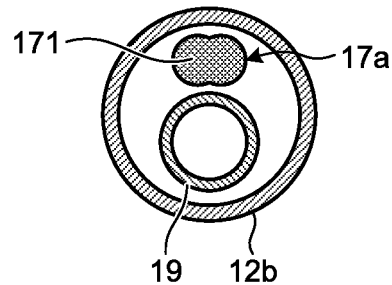
FIG. 5A is a cross-sectional view of the rigid endoscope main body corresponding to line A-A illustrated in FIG. 4.
Figure 5B:
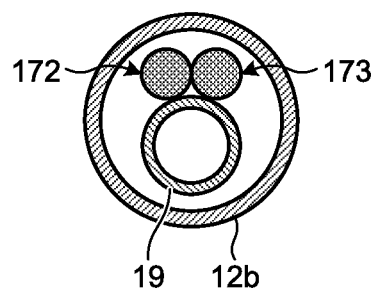
FIG. 5B is a cross-sectional view of the rigid endoscope main body corresponding to line B-B illustrated in FIG. 4.
Figure 5C:
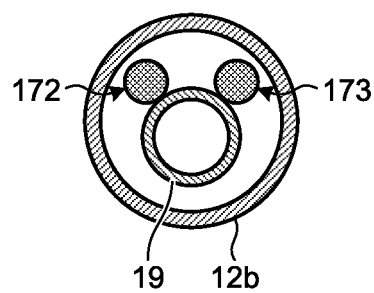
FIG. 5C is a cross-sectional view of the rigid endoscope main body corresponding to line C-C illustrated in FIG. 4.
Figure 5D:
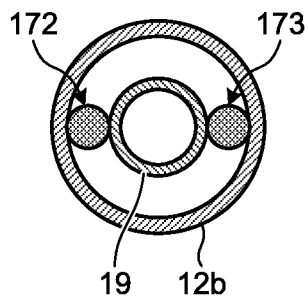
FIG. 5D is a cross-sectional view of the rigid endoscope main body corresponding to line D-D illustrated in FIG. 4.
Figure 5E:
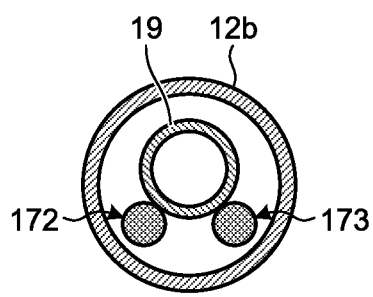
FIG. 5E is a cross-sectional view of the rigid endoscope main body corresponding to line E-E illustrated in FIG. 4.
Figure 5F:
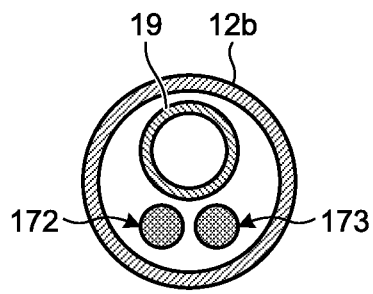
FIG. 5F is a cross-sectional view of the rigid endoscope main body corresponding to line F-F illustrated in FIG. 4.

In the following, an internal configuration of the rigid endoscope main body 11 will be described with reference to FIGS. 3 and 4 and FIG. 5A to FIG. 5F. FIG. 5A is a cross-sectional view of the rigid endoscope main body corresponding to line A-A illustrated in FIG. 4. FIG. 5B is a cross-sectional view of the rigid endoscope main body corresponding to line B-B illustrated in FIG. 4. FIG. 5C is a cross-sectional view of the rigid endoscope main body corresponding to line C-C illustrated in FIG. 4. FIG. 5D is a cross-sectional view of the rigid endoscope main body corresponding to line D-D illustrated in FIG. 4. FIG. 5E is a cross-sectional view of the rigid endoscope main body corresponding to line E-E illustrated in FIG. 4. FIG. 5F is a cross-sectional view of the rigid endoscope main body corresponding to line F-F illustrated in FIG. 4. Furthermore, FIG. 5A to FIG. 5F are diagrams each illustrating the arrangement of signal lines (signal line group) and the first channel 19, and a first tube 181 to a third tube 183, which will be described later, are not illustrated.

The signal cable 17 transmits the signal generated by the ultrasound transducer 15. The signal cable 17 includes, as illustrated in FIG. 3, a first cable portion 17a that forms a first signal line group 171 by collectively binding a plurality of signal lines (for example, signal lines 170 illustrated in FIG. 6) connected to a relay board 15a into a single bundle; a branching portion 17b that is continuously connected to the first cable portion 17a and that branches the plurality of signal lines into two bundles (a second signal line group 172 and a third signal line group 173); a second cable portion 17c in which each of the two signal line groups (the second signal line group 172 and the third signal line group 173) extends; a binding portion 17d that forms a fourth signal line group 174 by binding both the second signal line group 172 and the third signal line group 173; and a third cable portion 17e that extends on the grip portion 13 side by maintaining a single-bundle state from the binding portion 17d. The relay board 15a is electrically connected to the ultrasound transducer 15 and the signal cable 17. In the third cable portion 17e, an overall shield 175 is provided on an outer circumference formed by the plurality of signal lines, and a jacket 176 is provided on an outer circumference of the overall shield 175. Furthermore, an end portion of the third cable portion 17e on the side opposite to the binding portion 17d is connected to a connector (not illustrated) that is electrically connected to the universal cord 14 via the grip portion 13.

Furthermore, the signal cable 17 is provided with the first tube 181, a second tube 182, and the third tube 183 (see FIG. 3). Each of the first tube 181, the second tube 182, and the third tube 183 is formed using a heat shrinkable tube having insulation properties and cover, by causing heat shrinkage of the heat shrinkable tubes to occur, a part of the signal cable 17 including the overlapped regions of the adjacent tubes, specifically, an outer circumference of the signal line groups that are exposed between the insulation pipe 12e and the overall shield 175 in the signal cable 17. In the first embodiment, the first tube 181 and the third tube 183 that cover a part of the signal cable 17 corresponds to a tube according to the appended claims and, from among the signal cables 17, the second tube 182 that covers each of the branched signal line groups (the second signal line group 172 and the third signal line group 173) corresponds to a second tube according to the appended claims.

The first tube 181 covers a part of the first cable portion 17a including a part of the insulation pipe 12e, the branching portion 17b, and a part of the second cable portion 17c.

The second tube 182 covers each of the second signal line group 172 and the third signal line group 173. One end of the second tube 182 is covered by the first tube 181 and the other end of the second tube 182 is covered by the third tube 183. The second tube 182 is formed of a first cylindrical portion 1821, which extends along the second signal line group 172 and covers the second signal line group 172, and a second cylindrical portion 1822, which extends along the third signal line group 173 and covers the third signal line group 173.

The third tube 183 covers end portions of the second signal line group 172 and the third signal line group 173 on a side different from a side connected to the relay board 15a, the fourth signal line group 174 on a side connected to the second cable portion 17c, a part of the overall shield 175, and a part of the jacket 176.

An antifriction material is provided on the front surface of the signal cable 17 in order to prevent friction with an inner wall of the tubular portion 12b or internal objects. Specifically, conductive powder, such as carbon, that is an antifriction material is applied on the front surface of the first tube 181, the second tube 182, the third tube 183, and the jacket 176.

As described above, because the first channel 19 is provided so as to be inclined with respect to the axial direction of the first insertion portion 12, if the signal cable 17 is provided so as to extend parallel to the central axis of the first insertion portion 12, the signal cable 17 interferes with the first channel 19. Because of this, in the first embodiment, the first channel 19 is inserted into a vacant space that is formed by the extending second signal line group 172 and the third signal line group 173 branched at the signal cable 17, thereby preventing interference between the signal cable 17 and the first channel 19 (see FIG. 4).

Specifically, the first signal line group 171 (the first cable portion 17a) and the first channel 19 formed as a single bundle of signal lines are arranged, from the ultrasound transducer 15 side of the first insertion portion 12, side by side in the vertical direction in the drawing (see FIG. 5A). At this position, the first cable portion 17a is disposed on the ultrasound transducer 15 side and the first channel 19 is arranged on the opposite side thereof.

As approaching the grip portion 13 side from the arrangement illustrated in FIG. 5A, the second signal line group 172 and the third signal line group 173 branched by the branching portion 17b are moved in the directions opposite to each other along an outer circumference of the first channel 19 (see FIG. 5B to FIG. 5F). At this time, the first channel 19 gradually moves in an upward direction in the drawing along the inclination. The arrangement of the signal cable 17 and the first channel 19 is opposite to the arrangement illustrated in FIG. 5A before the binding portion 17d. Thereafter, the signal lines of the second signal line group 172 and the third signal line group 173 are collected together by the binding portion 17d. In this way, by dividing the signal lines of the signal cable 17 into two bundles, it is possible to change the arrangement of the signal cable 17 and the first channel 19, without increasing the diameter of the tubular portion 12b, while preventing interference between the signal cable 17 and the first channel 19.

Figure 6:
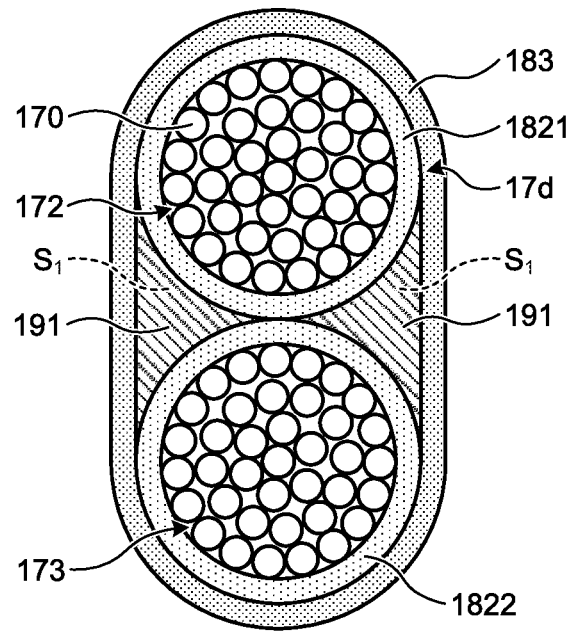
FIG. 6 is a cross-sectional view illustrating a configuration of a signal cable corresponding to line G-G illustrated in FIG. 3.

Subsequently, the configuration of the binding portion 17d of the signal cable will be described with reference to FIG. 6. FIG. 6 is a cross-sectional view illustrating a configuration of a signal cable corresponding to line G-G illustrated in FIG. 3. In the binding portion 17d, a vacant space $S_1$ is formed by both an outer circumferential surface of the second tube 182 (the first cylindrical portion 1821 and the second cylindrical portion 1822) that covers two signal line groups (the second signal line group 172 and the third signal line group 173) having a circular or an oval shaped outer circumference and an inner circumferential surface of the third tube 183. The antifriction material described above is provided on each of the second tube 182 and the third tube 183, which may possibly result in short circuits in the signal lines caused by the antifriction material entering into the third tube 183 via the vacant space $S_1$. In the first embodiment, a filling member 191 is filled in the vacant space $S_1$, which prevents the antifriction material from entering the third tube 183 via the vacant space $S_1$.

The filling member 191 is formed by solidifying a low melting point resin or wax. The low melting point resin mentioned here is a resin having a melting point at the temperature between 80° C. and 250° C., inclusive. The upper limit of 250° C. is the melting point of the resin that is used as the jacket 176 and it is preferable that the melting point of the low melting point resin be lower than the melting point of the jacket 176. The lower limit of the melting point may be set as long as it is higher than the highest temperature at a work area at the time of assembly and, in this embodiment, the lower limit of the melting point is set to 80° C. or above.

Examples of a low melting point resin include polyethylene, polypropylene, polystyrene, acrylonitrile-styrene (AS) resin, ABS resin, polyvinyl chloride (PVC), vinyl chloride resin, acrylic resin (for example, poly methyl methacrylate (PMMA) resin), methacrylic resin, polycarbonate, polyvinylidene fluoride, polyamide (nylon 12), Ethylene-Vinyl Acetate (EVA) copolymer resin, ethylene-methacrylic acid copolymer (EMMA), and polyolefin. Furthermore, it may also be possible to use a material obtained by mixing glass fiber or the low melting point resin described above into wax. Furthermore, by mixing pigment, it may also be possible to improve the visibility of the filling member 191 by changing a color.

After the filling member 191 is filled in the vacant space $S_1$ described above in a liquid state obtained by heating the filling member 191 at the temperature of melting point, the filling member 191 is solidified after the filling member 191 is cooled. At this time, because the filling member 191 is solidified by being brought into contact with the outer circumferential surface of the second tube 182 and the inner circumferential surface of the third tube 183, the filling member 191 is adhered between the second tube 182 and the third tube 183 in an in an airtight manner. In this way, the filling member 191 can fill the vacant space $S_1$ between the second tube 182 and the third tube 183. Furthermore, the resin may be cooled by cold air when the temperature of the resin becomes lower than the melting point or may be cooled by leaving the resin at a room temperature.

Furthermore, when the second tube 182 or the third tube 183 is removed due to maintenance of repair, the filling member 191 can be easily removed by liquefying by heating the filling member 191 at a temperature above the melting point, which makes it possible to simply perform an operation of removing the second tube 182 and the third tube 183 at the time of maintenance.

Furthermore, because the same vacant space is also generated between the first tube 181 and the second tube 182 in the branching portion 17b, the filling member 191 is provided.

Then, in the process of manufacturing the rigid endoscope main body 11 described above, when manufacturing the first insertion portion 12, first, one end side of the plurality of signal line, for which the overall shield 175 and the jacket 176 are provided on the one end side, are branched into two and then the third tube 183 before heat shrinkage is inserted from the other end side to the jacket 176.

Thereafter, the second tube 182 before heat shrinkage described above is inserted. Specifically, the second signal line group 172 is inserted into the first cylindrical portion 1821 and the third signal line group 173 is inserted into the second cylindrical portion 1822. After the signal line has been inserted into the second tube 182, the second signal line group 172 and the third signal line group 173 are inserted into the first tube 181 before heat shrinkage and the distal end component portion 12a in this order. At this time, the insulation pipe 12e is fitted into the mounting portion 12d of the distal end component portion 12a.

Thereafter, each of the signal lines of the first cable portion 17a is connected to the relay board 15a. At this time, the ultrasound transducer 15 may also previously be connected to the relay board 15a or, alternatively, the ultrasound transducer 15 may also be connected to the relay board 15a after having connected the plurality of signal lines to the relay board 15a. After the first cable portion 17a and the relay board 15a are connected, the ultrasound transducer 15 is accommodated in the mounting portion 12d of the distal end component portion 12a and then the ultrasound transducer 15 is bonded and fixed to the distal end component portion 12a.

Thereafter, positioning of the first tube 181 and the third tube 183 before heat shrinkage and the signal lines adjusted such that each of the first tube 181 and the third tube 183 covers a part of the second tube 182, and then the first tube 181, the second tube 182, and the third tube 183 are heated to cause heat shrinkage to occur so as to be crimped to the signal lines. Furthermore, it is preferable that the length of the overlapping portion in which each of the first tube 181 and the third tube 183 covers a part of the second tube 182 be set to be equal to or greater than 4 mm.

After the first tube 181, the second tube 182, and the third tube 183 are heated to cause heat shrinkage to occur, the liquid filling member 191 is poured into the vacant space between the first tube 181 and the second tube 182 and the vacant space (vacant space $S_1$) between the second tube 182 and the third tube 183 and solidified, whereby the filling member 191 is arranged in the vacant space between the tubes.

Thereafter, the first channel 19 is inserted into the vacant space formed by the second signal line group 172 and the third signal line group 173. Then, by inserting the signal cable 17 and the first channel 19 into the tubular portion 12b and by attaching the tubular portion 12b to the distal end component portion 12a, the first insertion portion 12 into which the signal cable 17 and the first channel 19 are inserted is formed.

According to the first embodiment described above, the vacant space, which is formed by two signal line groups (the second signal line group 172 and the third signal line group 173) obtained by branching the plurality of signal lines into to bundles, is inserted into the first channel 19. Furthermore, the filling member 191 made of a low melting point resin or wax is provided in the vacant space (vacant space $S_1$) that is generated between the two heat shrinkable tubes (between the first tube 181 and the second tube 182 and between the second tube 182 and the third tube 183) that are provided in the branching portion 17b and binding portion 17d that are the branching sections of the signal line group, so that the vacant space between the heat shrinkable tubes are filled. Consequently, it is possible to reduce the diameter of the first insertion portion 12 and easily perform an operation at the time of maintenance or repair while suppressing the friction generated in the cables.

Furthermore, according to the first embodiment as described above, the binding portion 17d binds the end portions of the signal cable 17 on a side opposite to the distal end component portion 12a side into a single bundle. Consequently, when compared to the two-bundle state, it is possible to improve the performance of operation of inserting the signal cable 17 into the tubular portion 12b at the time of manufacturing an endoscope.

Furthermore, according to the first embodiment as described above, because the signal line groups exposed between the distal end component portion 12a and the overall shield 175 are covered by the heat shrinkable tubes (the first tube 181, the second tube 182, and the third tube 183) having insulation properties, it is possible to ensure insulation properties of the signal line groups. In particular, the branching section (the binding portion 17d) of the signal line group is covered by the second tube 182 and the third tube 183 overlapping with each other. Consequently, it is possible to reliably ensure the insulation property in the branching section.

Furthermore, in the first embodiment as described above, a case has been described in which the positions of the first tube 181 and the third tube 183 are adjusted; the first tube 181, the second tube 182, and the third tube 183 before heat shrinkage are heated to cause heat shrinkage to occur; and then the plurality of signal lines are covered. However, it may be possible to heat a region in which the tubes overlap with each other, such as the region in which the first tube 181 and the second tube 182 overlap with each other, the region in which the second tube 182 and the third tube 183 overlap with each other, and the region in which the filling member 191 is arranged, in order to cause heat shrinkage to occur in only the region in which the tubes overlap.

Furthermore, in the first embodiment described above, markers indicating arrangement positions of the first tube 181 and the third tube 183 with respect to the second tube 182 may also be provided on the second tube 182 (the second tube before heat shrinkage). Consequently, it is possible to arrange the first tube 181 and the third tube 183 before heat shrinkage while checking the positions with respect to the second tube before heat shrinkage.

Furthermore, in the first embodiment described above, a case has been described in which a part of the signal cable 17 is branched into two; however, the signal cable 17 may also be branched into three or more. In this case, a filling member is provided in the vacant space that is formed at each of the branching sections.

First Modification of First Embodiment

Figure 7:
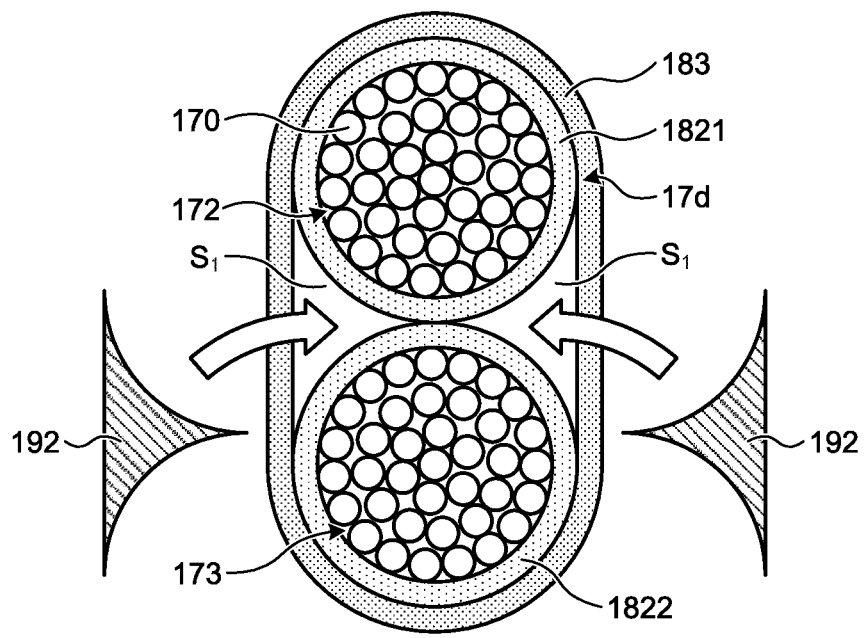
FIG. 7 is a cross-sectional view illustrating a configuration of a signal cable of a rigid endoscope main body according to a first modification of the first embodiment.

In the first embodiment described above, a case has been described in which the filling member 191 is formed by heating at the melting point or above to obtain the liquid-state filling member 191, by filling the filling member 191 in the vacant space $S_1$, and by cooling and solidifying the filling member 191; however, a previously shaped filling member may also be fitted into the vacant space $S_1$. FIG. 7 is a cross-sectional view illustrating a configuration of a signal cable of a rigid endoscope main body according to a first modification of the first embodiment.

In the first modification, a filling member 192 illustrated in FIG. 7 is previously shaped and is fitted in the vacant space $S_1$ provided between the second tube 182 and the third tube 183, thereby filling the vacant space $S_1$ between the second tube 182 and the third tube 183. The filling member 192 has a shape in accordance with the vacant space $S_1$ and is shaped by using the above described low melting point resin, the wax, and a mixture of wax and the low melting point resin.

According to the first modification, by previously shaping the filling member 192 and by fitting the filling member 192 in the vacant space $S_1$ generated between the second tube 182 and the third tube 183, it is possible to improve workability when compared to the case in which, as described above in the first embodiment, a liquid resin is filled and solidified.

Second Modification of First Embodiment

Figure 8:
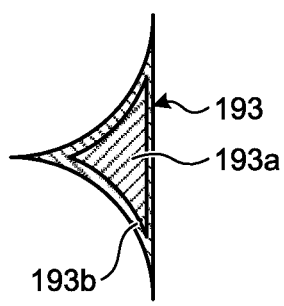
FIG. 8 is a cross-sectional view illustrating a configuration of a relevant part of a rigid endoscope main body according to a second modification of the first embodiment.

In the first modification described above, a case has been described in which the filling member 192 is shaped by using a low melting point resin; however, the filling member may also be shaped by using resins at different melting points. FIG. 8 is a cross-sectional view illustrating a configuration of a relevant part of a rigid endoscope main body according to a second modification of the first embodiment and illustrates a cross section of the filling member.

In the second modification, similarly to the first modification described above, by previously shaping a filling member 193 illustrated in FIG. 8 and filling the filling member 193 in the vacant space $S_1$ (for example, see FIG. 7) between the second tube 182 and the third tube 183, thereby filling the vacant space $S_1$ between the second tube 182 and the third tube 183.

The filling member 193 is made of two types of resins (a low melting point resin and a high melting point resin) having relatively different melting points. Specifically, the filling member 193 includes an inner part resin 193a, which is made of a high melting point resin and provided inside the filling member 193, and an outer part resin 193b, which is made of a low melting point resin and covers the front surface of the inner part resin 193a. The outer part resin 193b is shaped by using the above described low melting point resin, the wax, and the mixture of the wax and the low melting point resin. Any material may be used for the inner part resin 193a as long as a material with a melting point higher than that used for the outer part resin 193b is used. It is preferable to use resins having the similar type for the inner part resin 193a and the outer part resin 193b from the viewpoint of increasing the adhesiveness between the inner part resin 193a and the outer part resin 193b. For example, when low melting point polyethylene is used for the outer part resin 193b, it is preferable to use high melting point polyethylene for the inner part resin 193a.

The filling member 193 is arranged in the vacant space $S_1$ described above and is heated to a temperature equal to or higher than the melting point of the low melting point resin and lower than the melting point of the high melting point resin to liquefy only the liquid outer part resin 193b. Thereafter, the filling member 193 is cooled to solidify the outer part resin 193b. At this time, because the outer part resin 193b is tightly brought into contact with, due to the liquefaction, for example, the outer circumferential surface of the second tube and the inner circumferential surface of the third tube 183, the gap between the second tube 182 and the third tube 183 are adhered in an airtight manner. In this way, the filling member 193 can fill the vacant space $S_1$ between the second tube 182 and the third tube 183. Furthermore, the filling member 193 in which only the outer part resin 193b was liquefied may also be arranged in the vacant space $S_1$ and then solidified.

According to the second modification, after the filling member 193 is previously shaped and arranged in the vacant space $S_1$ between the second tube 182 and the third tube 183, only the outer part resin 193b is liquefied and then solidified. Consequently, it is possible to improve workability when compared to a case in which, similarly to the first embodiment described above, a resin is poured and solidified and it is possible to improve adhesiveness between the tubes when compared to the first modification described above.

Second Embodiment

Figure 9:
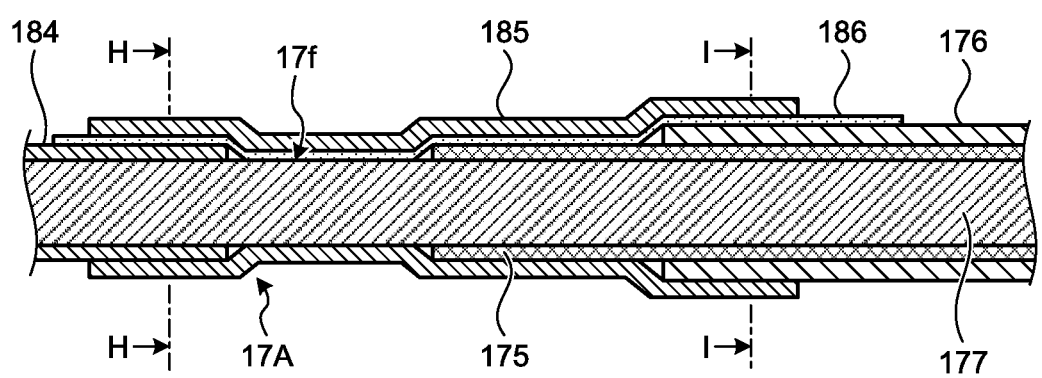
FIG. 9 is a diagram illustrating a configuration of a part of a signal cable of a rigid endoscope main body according to a second embodiment.
Figure 10:
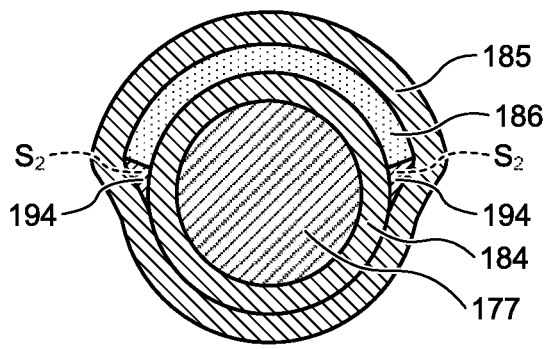
FIG. 10 is a cross-sectional view illustrating a configuration of a signal cable corresponding to line H-H illustrated in FIG. 9.
Figure 11:
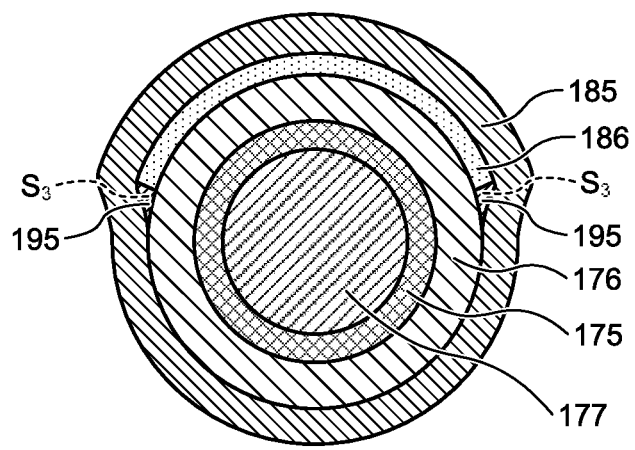
FIG. 11 is a cross-sectional view illustrating a configuration of a signal cable corresponding to line I-I illustrated in FIG. 9.

In the first embodiment described above, a case has been described in which a part of the signal cable 17 is branched into two bundled of signal line groups and a filling member is provided in the vacant space formed between the tubes that cover the signal line groups at the branching section; however, even if a single bundle of extending signal line group is used, a vacant space may possibly be generated between the tube depending on the covering state of the tube, thereby filling is needed. FIG. 9 is a diagram illustrating a configuration of a part of a signal cable of a rigid endoscope main body according to a second embodiment. FIG. 10 is a cross-sectional view illustrating a configuration of a signal cable corresponding to line H-H illustrated in FIG. 9. FIG. 11 is a cross-sectional view illustrating a configuration of a signal cable corresponding to line I-I illustrated in FIG. 9.

A signal cable 17A according to the second embodiment includes, as illustrated in FIG. 9, a signal line group 177 constituted by a plurality of signal lines as a single bundle. The overall shield 175 and the jacket 176 are provided on a part of the outer surface of the signal line group 177. The signal cable 17A is provided with an exposed portion 17f that is used to expose the signal line group 177 from both the overall shield 175 and the jacket 176 for the wiring performed on the relay board 15a of the signal lines or the connector. The front surface of the signal line group 177 exposed at the exposed portion 17f is covered by a fourth tube 184 and a fifth tube 185 that are heat shrinkable tubes. Furthermore, an insulating tape 186 is provided between the fourth tube 184 and the fifth tube 185 around half of the circumference of the signal line group 177 in the circumferential direction (see FIG. 10). In the second embodiment, the fifth tube 185 that covers a part of the signal cable 17A corresponds to a tube according to the appended claims. The vacant space formed between the signal cable 17A and the tube (the fifth tube 185) corresponds to the vacant space formed between the fourth tube 184, the fifth tube 185, and the insulating tape 186 and corresponds to the vacant space formed between the jacket 176, the fifth tube 185, and the insulating tape 186.

The fourth tube 184 extends, at the exposed portion 17f, on a side opposite to the overall shield 175, i.e., on the end portion side that is connected to the relay board 15a or the connector.

The insulating tape 186 covers a part of the end portion of the jacket 176, a part of the exposed portion from the jacket 176 of the overall shield 175, and a part of the end portion of the fourth tube 184.

The fifth tube 185 covers a part of the end portion of the jacket 176, a part of the exposed portion from the jacket 176 of the overall shield 175, a part of the end portion of the fourth tube 184, and the insulating tape 186 other than both ends thereof.

When the fifth tube 185 of the signal cable 17A is removed at the time of maintenance or repair of the signal cable 17A, an incision is made in the fifth tube 185 using a blade, such as a cutter, at the arrangement position of the insulating tape 186. Consequently, the fifth tube 185 can be removed without damaging the signal line group 177, the overall shield 175, the jacket 176, and the fourth tube 184. It is preferable that the insulating tape 186 be provided by being exposed from the fifth tube 185 such that the arrangement position of the insulating tape 186 can be visually recognized.

In the signal cable 17A having the configuration described above, because the insulating tape 186 is provided by a length corresponding to half of the circumference of the signal cable 17A, a vacant space $S_2$ is formed by the outer surface of the fourth tube 184, the inner surface of the fifth tube 185, and the surface on the insulating tape 186 side. Similarly, in the signal cable 17A, a vacant space $S_3$ is formed by the outer surface of the jacket 176, the inner surface of the fifth tube 185, and the surface on the insulating tape 186 side.

Similarly to the first embodiment described above, if an antifriction material enters the fifth tube 185 via the vacant spaces $S_2$ and $S_3$, short circuits may possibly occur between the signal lines; therefore, in the second embodiment, filling members 194 and 195 are provided in the corresponding vacant space.

The filling members 194 and 195 are provided, as illustrated in FIGS. 10 and 11, in the vacant spaces $S_2$ and $S_3$, respectively. The filling members 194 and 195 are shaped by using the above described low melting point resin, the wax, and the mixture of the wax and the low melting point resin. The filling members 194 and 195 may also be provided in the vacant spaces $S_2$ and $S_3$ in a liquid state as described above in the first embodiment and then solidified thereafter; may also be disposed in the vacant spaces $S_2$ and $S_3$ in a previously shaped manner as described in the first modification; or may also be made of resins having different melting points as described in the second modification.

According to the second embodiment described above, the insulating tape that is used to prevent damage at the time of maintenance or repair is provided around half of the circumference of the signal cable 17A; the fifth tube 185 that is a heat shrinkable tube is provided on the outer surface of the insulating tape 186; and the filling members 194 and 195 made of a low melting point resin or wax is provided in the vacant spaces (vacant spaces $S_2$ and $S_3$) that are generated by the insulating tape 186 and is filled in the vacant space between the heat shrinkable tubes. Consequently, it is possible to easily perform an operation at the time of maintenance or repair while preventing damage by suppressing friction generated between the cables.

Furthermore, the second embodiment can be applicable to, in addition to a rigid endoscope, a signal cable inserted into the insertion portion of a flexible endoscope. In particular, the insertion portion of the flexible endoscope is flexible and a tube is also deformed due to deformation of the insertion portion. At this time, a vacant space is generated between the tubes; however, by disposing the filling member, it is possible to prevent the antifriction material from entering from the vacant space generated between the tubes, thereby ensuring the fixing between the tubes. If the tubes are reliably fixed, it is possible to prevent relative positional deviation between the tubes.

At this time, if autoclave is performed on a flexible endoscope, in order to acquire resistance to the temperature at the time of autoclave, it is preferable that the melting point of a low melting point resin be between 140° C. and 250° C., inclusive.

Modification of Second Embodiment

Figure 12:
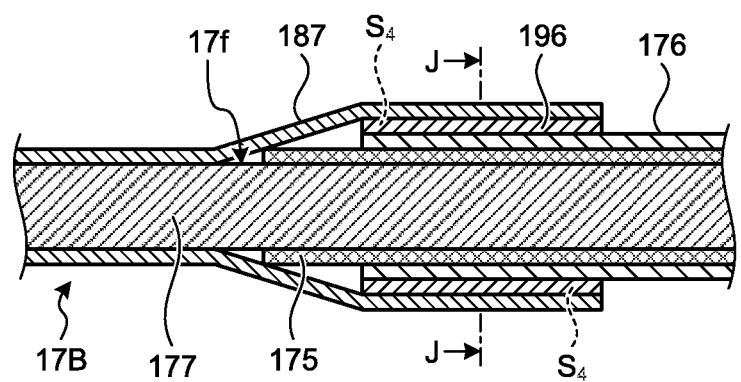
FIG. 12 is a cross-sectional view illustrating a configuration of a signal cable of a rigid endoscope main body according to a modification of the second embodiment.
Figure 13:
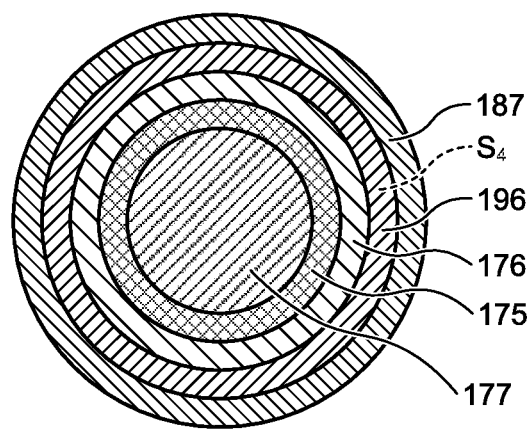
FIG. 13 is a cross-sectional view illustrating a configuration of a signal cable corresponding to line J-J illustrated in FIG. 12.

In the second embodiment described above, a case has been described in which, in the signal line group extending as a single bundle, a filling member is provided in the vacant space generated due to deformation of the fifth tube 185 caused by the insulating tape 186 is provided in order to prevent an antifriction material from entering; however, even if the insulating tape 186 is not disposed and the signal cable is concentrically provided, a filling member may also be disposed if there is a vacant space generated by a difference between the length of the circumferences of a circle. FIG. 12 is a cross-sectional view illustrating a configuration of a signal cable of a rigid endoscope main body according to a modification of the second embodiment. FIG. 13 is a cross-sectional view illustrating a configuration of a signal cable corresponding to line J-J illustrated in FIG. 12.

A signal cable 17B according to the modification of the second embodiment includes, as illustrated in FIG. 12, the signal line group 177 formed of a plurality of signal lines as a single bundle and is provided with the overall shield 175 and the jacket 176 on the outer surface of the signal line group 177. The signal cable 17B is provided with an exposed portion 17*f* that is used to expose the signal line group 177 from the overall shield 175 and the jacket 176 in order to perform wiring of the signal lines on the relay board 15*a* or a connector. The front surface of the signal line group 177 exposed at the exposed portion 17*f* is covered by a sixth tube 187 that is a heat shrinkable tube. In the modification of the second embodiment, the sixth tube 187 that covers a part of the signal cable 17B corresponds to a tube according to the appended claims and the vacant space formed between the signal cable 17B and the tube (the sixth tube 187) corresponds to the vacant space formed between the jacket 176 and the sixth tube 187.

The sixth tube 187 covers a part of the end portion of the jacket 176, a part of the exposed portion exposed from the jacket 176 of the overall shield 175, and a part of the signal line group 177.

In the signal cable 17B having the configuration described above, for example, if the length of the circumference of the outer surface of the jacket 176 is smaller than that of the inner surface of the sixth tube 187, a vacant space $S_4$ is formed between the outer surface of the jacket 176 and the inner surface of the sixth tube 187.

Similarly to the first embodiment described above, if an antifriction material enters the sixth tube 187 via the vacant space $S_4$, short circuits may possibly occur between the signal lines, in also the modification of the second embodiment, a filling member 196 is provided in the vacant space $S_4$. Furthermore, the filling member 196 also functions as a fixing portion member for preventing positional deviation between the jacket 176 and the sixth tube 187. In particular, in a case of a flexible endoscope, a signal cable is bent when compared to the first insertion portion 12 in the rigid endoscope main body 11 and thus stress applied to the overlapping portion of the jacket 176 and the sixth tube 187 is increased; therefore, by providing the filling member 196, it is possible to prevent positional deviation due to the stress.

The filling member 196 is provided in the vacant space $S_4$, as illustrated in FIGS. 12 and 13. The filling member 196 has a cylindrical shape and is shaped by using the above described low melting point resin, the wax, and the mixture of the wax and the low melting point resin. The filling member 196 may also be provided in, similarly to the first embodiment described above, the vacant space $S_4$ in a liquid state; may also be disposed in the vacant space $S_4$ in a previously shaped manner as described in the first modification; or may also be made of resins having different melting points as described in the second modification.

According to the modification of the second embodiment described above, in the signal cable 17B, the filling member 196 made of a low melting point resin or wax is provided in the vacant space $S_4$ generated between the outer surface of the jacket 176 and the inner surface of the sixth tube 187, thereby filling a vacant space between the heat shrinkable tubes. Consequently, it is possible to easily perform an operation at the time of maintenance or repair while preventing damage by suppressing friction generated between the cables. Furthermore, according to the modification of the second embodiment, because the filling member 196 has a cylindrical shape, the filling member 196 can be bonded and fixed around the entire circumference, which makes it possible to ensure airtightness.

Furthermore, in the modification of the second embodiment, the filling member 196 may also be formed in the shape of sheet and disposed. Consequently, it is possible to fix the portion between the outer surface of the jacket 176 and the inner surface of the sixth tube 187 at a uniform interval and thus reduce the diameter.

Furthermore, in the modification of the second embodiment, the filling member 196 may also be a heat shrinkable tube. In this case, it is preferable that the heat shrinkable tube be made of a material having the same melting point as that of the low melting point resin described above. Consequently, it is possible to fix the portion between the outer surface of the jacket 176 and the inner surface of the sixth tube 187 at a uniform interval and thus reduce the diameter.

The embodiments have been described above; however, the present disclosure is not limited to only the embodiments and modifications described above. The present disclosure is not limited to the embodiments and modifications as described above, and various embodiments may be made within the scope not departing from the technical concept as defined by the appended claims. In addition, configurations of the embodiments and modifications may also be combined appropriately.

Furthermore, according to the first and second embodiments described above, the piezoelectric element has been described as an example of a device that outputs an ultrasound wave and converts an ultrasound wave entered from outside into an echo signal; however, the embodiments are not limited to this example. It may be possible to use a device manufactured using microelectromechanical systems (MEMS), such as capacitive micromachined ultrasonic transducers (C-MUTs).

Furthermore, according to the first and second embodiments described above, the ultrasound endoscope that observes the interior of the subject via the urethra has been described. However, a device that is inserted into, in addition to the urethra, a biliary tract, a bile duct, a pancreatic duct, a trachea, a bronchus, or a ureter and observes surrounding organs (a pancreas, lungs, a bladder, lymph nodes, and the like).

Furthermore, according to the first and second embodiments described above, the ultrasound endoscope has been described as an example; however, the embodiments are not limited to this example as long as the endoscope includes a signal cable for transmitting an image signal. For example, the present disclosure is applicable to an oral endoscope that is inserted into a digestive tract (an esophagus, a stomach, a duodenum, or a large intestine) or a respiratory organ (a trachea or a bronchus) of the subject and captures an image of digestive tracts and respiratory organs, that is, the oral endoscope provided with a flexible insertion portion that includes an imaging element serving as an image sensor. In particular, the present disclosure is useful for an endoscope provided with an image sensor, such as a charge coupled device (CCD) used for a high-speed camera, that includes a cable having a large number of signal lines and requiring an insulation process.

According to the present disclosure, an advantage is provided in that it is possible to easily perform an operation at the time of maintenance or repair while preventing friction generated in the cable.

As described above, the endoscope according to the present disclosure is useful for easily performing an operation at the time of maintenance or repair while reducing friction generated in cables.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an insertion portion to be inserted into a subject;
   an image sensor provided at a distal end of the insertion portion and configured to acquire an image of the subject;
   a signal cable connected to the image sensor at one end of the signal cable, the signal cable including a signal line group formed of a plurality of signal lines configured to transmit signals acquired by the image sensor;
   a tube provided at a part of the signal cable, the tube covering the signal cable and having insulation properties;
   a tape provided between an outer surface of the signal cable and an inner surface of the tube, the tape being provided in an arc shape that follows an outer contour of the signal cable; and
   a filling material configured to fill a vacant space formed among the signal cable, the tape and the tube and at least a part of which is made of a material with a low melting point.

2. The endoscope according to claim 1, wherein the filling is material made of the material with the low melting point is one of a low melting point resin, a wax, a glass fiber and a mixture of the wax and the low melting point resin.

3. The endoscope according to claim 2, wherein the melting point of the low melting point resin is 80° C. to 250° C.

4. The endoscope according to claim 2, wherein the filling material has a sheet shape and fills the vacant space that forms a ring-shaped space area.

5. The endoscope according to claim 2, wherein the filling material has a cylindrical shape and fills the vacant space that forms a ring-shaped space area.

6. The endoscope according to claim 1, wherein
   the signal cable includes two signal line groups formed by branching the plurality of signal lines into two,
   the endoscope further comprises second tubes each of which covers the corresponding one of the two signal line groups and has insulation properties, and
   the filling material further fills the vacant space formed between the tube and the second tubes.

7. The endoscope according to claim 1, wherein the filling material has a shape in accordance with a shape of the vacant space formed among the signal cable, the tape and the tube.

8. The endoscope according to claim 7, wherein
   the filling material includes
      an inner part resin provided at an inner part side of the filling material, and
      an outer part resin configured to cover an outer surface of the inner part resin and provided at an outer part side of the filling material, and
   a melting point of the inner part resin is higher than a melting point of the outer part resin.

9. The endoscope according to claim 1, wherein the filling material is a heat shrinkable tube made of a low melting point resin.

10. The endoscope according to claim 1, wherein the tape has an insulation property.

11. The endoscope according to claim 1, wherein the signal cable comprising:
    an exposed portion where the signal line is exposed near the one end, and
    a second tube provided between the exposed portion and the one end and configured to cover the signal line group, and
    the vacant space is formed by an outer surface of the second tube, the inner surface of the tube, and the tape.

12. A method of repairing an endoscope, the method comprising:
    heating a filling material filled in a vacant space formed among a signal cable, a tape provided between an outer surface of the signal cable and an inner surface of the tube in an arc shape that follows an outer contour of the signal cable, and a tube covering the signal cable to liquidize the filling material, the signal cable being connected to an image sensor;
    replacing the tube with a replacement tube;
    filling the filling material in the vacant space; and
    fixing the replacement tube by heating and cooling the filling material.

* * * * *